(12) United States Patent
Ogle

(10) Patent No.: US 6,863,066 B2
(45) Date of Patent: Mar. 8, 2005

(54) ADJUSTABLE NASAL DILATOR FILTER

(76) Inventor: Ronald Jack Ogle, 1723 St. Ives Blvd., Alcoa, TN (US) 37701

( * ) Notice: Subject to any disclaimer, the term of this patent is extended or adjusted under 35 U.S.C. 154(b) by 0 days.

(21) Appl. No.: 10/350,245

(22) Filed: Jan. 23, 2003

(65) Prior Publication Data
US 2003/0144684 A1 Jul. 31, 2003

Related U.S. Application Data

(60) Provisional application No. 60/352,387, filed on Jan. 28, 2002.

(51) Int. Cl.⁷ .............................................. A61M 15/00
(52) U.S. Cl. ............................. 128/200.24; 128/206.11; 606/199
(58) Field of Search ....................... 128/200.24, 206.11, 128/202.25; 606/199, 204.45

(56) References Cited

U.S. PATENT DOCUMENTS

| | | | | |
|---|---|---|---|---|
| 406,580 | A | * 7/1889 | Guyot | 128/206.11 |
| 851,048 | A | * 4/1907 | Woodward | 606/199 |
| 1,077,574 | A | * 11/1913 | Woodward | 606/199 |
| 1,135,675 | A | * 4/1915 | Dixon | 606/199 |
| 1,255,578 | A | * 2/1918 | Boxley | 606/199 |
| 1,481,581 | A | * 1/1924 | Woodward | 606/199 |
| 1,597,331 | A | * 8/1926 | Thurston | 606/199 |
| 1,672,591 | A | * 6/1928 | Wells | 606/199 |
| 1,709,740 | A | * 4/1929 | Rogers | 606/199 |
| 1,743,993 | A | 1/1930 | Washigton | |
| 2,243,360 | A | * 5/1941 | Slatis | 128/206.11 |
| 2,282,681 | A | * 5/1942 | Stotz | 128/206.11 |
| 2,509,157 | A | 5/1950 | Lind | |
| 2,515,756 | A | * 7/1950 | Bove | 606/199 |
| 3,460,533 | A | 8/1969 | Madrazo | |
| 3,710,799 | A | * 1/1973 | Caballero | 606/199 |
| 3,828,577 | A | * 8/1974 | Haynes | 63/33 |
| 4,201,217 | A | 5/1980 | Slater | |
| 4,378,802 | A | 4/1983 | Ersek | |
| 4,414,977 | A | * 11/1983 | Rezakhany | 606/199 |
| 4,736,741 | A | * 4/1988 | Payton et al. | 128/207.18 |
| 4,759,365 | A | * 7/1988 | Askinazy | 606/199 |
| 5,479,944 | A | 1/1996 | Petruson | |
| 5,533,499 | A | 7/1996 | Johnson | |
| 5,533,503 | A | 7/1996 | Doubek et al. | |
| 5,549,103 | A | 8/1996 | Johnson | |
| D375,552 | S | 11/1996 | Davi | |

(List continued on next page.)

FOREIGN PATENT DOCUMENTS

| | | |
|---|---|---|
| CH | 686224 | 2/1996 |
| EP | 0 824 015 A2 | 2/1998 |
| EP | 0 958 798 A1 | 11/1999 |
| FR | 1341906 | 11/1963 |
| FR | 2631229 | 11/1989 |
| JP | 2001/009034 | 1/2001 |
| WO | WO 87/05798 | 10/1987 |
| WO | WO 99/55404 | 11/1999 |

*Primary Examiner*—Aaron J. Lewis
(74) *Attorney, Agent, or Firm*—Luedeka, Neely & Graham, P.C.

(57) ABSTRACT

A adjustable nasal dilator filter incorporating unique insertable symmetrical loops with electrical and mechanical design features for improving breathing, air filtration, sleep and snoring which is adjustable, self adjusting, re-useable, comfortable, safe, economical and uses no drugs or adhesives. The device consists of two symmetric polymer loops formed by a retaining tube. The, material, size, configuration, and electrical characteristics of these loops was designed to improve nasal air filtration as well as reshape and strengthen the internal nasal breathing passageways in order to provide the stated positive benefits. The interface with the nostrils and combined functionality of this device including the air filtration feature and universal adjustability makes this device unique and superior to prior art.

17 Claims, 1 Drawing Sheet

U.S. PATENT DOCUMENTS

| | | |
|---|---|---|
| D380,264 S | 6/1997 | Petruson |
| 5,665,104 A | 9/1997 | Lee |
| 5,706,800 A | 1/1998 | Cronk et al. |
| 5,713,833 A | 2/1998 | Milligan |
| 5,727,543 A * | 3/1998 | Corsaro ................ 128/200.24 |
| 5,775,335 A | 7/1998 | Seal |
| 5,816,241 A * | 10/1998 | Cook ................ 128/200.24 |
| 5,890,491 A | 4/1999 | Rimkus |
| 5,947,119 A | 9/1999 | Reznick |
| 6,004,342 A | 12/1999 | Filis |
| 6,270,512 B1 * | 8/2001 | Rittmann ................ 606/199 |
| 6,540,766 B2 * | 4/2003 | Martino ................ 606/199 |

* cited by examiner

ADJUSTABLE NASAL DILATOR FILTER

CROSS-REFERENCE TO RELATED APPLICATIONS

This application claims the benefit of Provisional Application Ser. No. 60/352,387, filed Jan. 28, 2002.

STATEMENT REGARDING FEDERALLY SPONSORED RESEARCH OR DEVELOPMENT

"Not Applicable"

REFERENCE TO MICROFICHE APPENDIX

"Not Applicable"

BACKGROUND OF INVENTION

The present invention relates to nasal filtration, dilating, and breathing devices.

Every year millions of individuals spray chemicals into their nostrils and attach devices to their noses in an attempt to improve nasal breathing. A large percentage of the human population experience periodic nasal air passage restrictions resulting from sinus irritations, changes in barometric pressure, nasal structure and other causes. This condition is particularly annoying at night and often causes poor air filtration, disrupted sleep patterns, excessive breathing through the mouth, dry mouth, snoring, and other discomforts and health problems. Millions of dollars are spent each year on drugs and remedies to deal with this condition. People seeking a non-drug related solution to this problem have no option except some type of mechanical device or appliance. My Nasal Dilator Filter is the only single mechanical device that improves nasal breathing, air filtration, and the above stated conditions. There is currently no prior art that addresses all of these issues. Prior art has attempted to deal with these issues by applying devices to both the outside of the nose and by inserting devices into the nasal cavities. My invention is a simple adjustable, reusable nasal insert device.

Prior art mechanical nasal dilators and filtration devices can generally be classified as external or insertable. One example of the external type art is U.S. Pat. No. 5,549,103 by Johnson, granted Aug. 27, 1996. This type art attaches a flat spring to the outside of the nose with adhesives. In spite of several disadvantages this prior art has gained popularity and market success because it is somewhat effective and has virtually no competition. Some of the disadvantages of this external prior art includes; skin irritation, skin discoloration, allergic reactions, not adjustable, uncomfortable, expensive, not reusable and does not accommodate the wide variety of nose sizes and configurations. These devices can be put on one time and cannot be reused or readjusted. If they are put on wrong they must be removed and disposed. In addition, the force and contact of the spring across the bridge of the nose causes discomfort.

There have also been a number of attempts to develop insertable internal nasal devices, appliances or dilators to improve nasal breathing including: U.S. Pat. No. 5,727,543 by Lugi Corsaro, granted Mar. 17, 1998 entitled NASAL BREATHING DEVICE; U.S. Pat. No. 1,255,578 by George Boxley, granted Feb. 5, 1918 entitled NASAL APPLIANCE; U.S. Pat. No. 1,481,581 by H. R. Woodward, granted Jan. 22, 1924, entitled NOSTRIL EXPANDER; U.S. Pat. No. 5,479,944 by Bjorn Petruson, granted Jan. 2, 1996 entitled NASAL DEVICES; U.S. Pat. No. 4,414,977 by Saeed Rezakhany, granted Nov. 15, 1983 entitled NASAL DILATOR; U.S. Pat. No. 4,201,217 by Robert L. Slater, granted May 6, 1980 entitled NOSTRIL EXPANDER; U.S. Pat. No. 4,759,365 by Leo Askinazy, granted Jul. 26, 1988 entitled SPRING COIL WIRE DEVICE; and U.S. Pat. No. 3,710,799 by Carlos Ramos Caballero, granted Jan. 16, 1973 entitled NOSE DILATOR. These devices have had limited or no commercial success in part due to significant disadvantages and design, development, or commercialization problems. Common Problems with these insertable prior art include; not comfortable, does not consider the wide variety of nose shapes and sizes, not adjustable, irritating, and not effective. In addition, most of these devices actually reduce nasal air filtration efficiency.

Air quality is becoming a problem of ever increasing concern. The air we breathe, particularly in our bedroom at night, often contains many particles and contaminants which cause allergic reactions and health problems. Our nasal cavity is designed to filter many of these contaminants but the efficiency of filtration is diminished in a large percentage of individuals due to allergies and configuration of the nasal cavity. Much of the contaminants including bacteria processed through the nostrils are captured and combined with mucus and either neutralized in the stomach or expelled from the nose. If these contaminants are breathed through the mouth many go strait to the lungs. The lungs cannot neutralize these contaminants as effectively as the stomach and more severe health problems can result. Unlike prior art, my dilator filter improves both nasal breathing and filtration thereby promoting better health.

There are also some insertable nasal air filtration art similar to disclosure U.S. Pat. No. 5,890,491, disclosing a Nose Filter. These and similar art filters do not decrease nasal air flow resistance. In fact, in many cases these devices actually increase air resistance and reduce the effective natural filtration surface inside the nose.

My nasal dilator filter provides an alternative to those who wish to use a mechanical device to improve nasal breathing and filtration. In addition, my invention does not have the disadvantages of the external nasal dilator. My invention addressed all of the disadvantages of prior art. In addition, none of the prior art provides the combined effects of my invention. My dilator filter has two uniquely designed adjustable loops for insertion into the nostrils. It was developed to incorporate a number of design and operational features to provide advantages over prior art. These advantages include:

a. Improved Sleep—Many individuals have a restriction near the nasal passage entrance that results in sleep pattern disruption. This condition is worsened by allergies and air pollution and is most noticeable at night. This restriction causes excessive breathing through the mouth which promotes dry mouth, snoring, and in some cases depravation of oxygen. My invention improves sleep by reducing nasal air flow resistance and promoting more nasal breathing, cleaner air intake, more oxygen and less breathing through the mouth.

b. Reduced air resistance through nasal passages—My invention uses two mechanisms to reduce nasal air resistance. When inserted my invention provides a nasal cavity form which tends to round out the vestibule thereby increasing the cross sectional airflow area. In addition the special configuration of the inserts provide shape and rigidity to the outside surface of the vestibule preventing restriction of the airflow passage during nasal breathing.

c. Increased nasal filtration efficiency—My invention improves nasal filtration efficiency in four ways. First, it makes a slight change in the configuration of the nasal cavity to increase the effective filtration area of the nasal cavity. Secondly, it provides an electrical charge to many of the contaminants to improve the efficiency of collection by the cilia and mucus in the nasal cavity. The charge is created materials that readily give up their electrons to other materials or particles. Particles that become negatively charged will be attracted to the positively charged cilia and surface inside the nasal cavity. The material in the air path will also attract particles in the air entering the nasal cavity. Thirdly, it promotes more nasal breathing such that contaminants can be processed in a more effective way. Fourthly, the nylon loop at the entrance to the nasal cavity will create a change in the air flow pattern which will result in more particles coming in contact with the walls of the nasal cavity and being captured and filtered.

d. Comfort to user—The prior art has significant disadvantages in this area. The external mechanical dilator concentrates a compression operation force on the bridge of the nose and tension forces on the outer skin of the nose in order to operate. These forces are applied to the outside of the nose with a strong adhesive. Current art that inserts in the nasal cavity does not readily accommodate the wide variety of nose sizes and configurations. In addition the configuration, force distribution and contact areas within the nasal cavity of these devices result in significant discomfort to the users. Comfort was a prime consideration for this invention. The configuration, size, material properties and placement inside the vestibule were determined to maximize user comfort.

e. Drug Free—Drug related dilators can have serious side effects. This invention was specifically designed to reduce nasal air resistance without the use of drugs.

f. Adhesive Free—Some of the prior art mechanical dilators utilize adhesives to attach a spring to the outside of the nose to separate the outer nasal tissue from the inner tissue. This adhesive can cause skin discoloration, irritation, and allergic reactions.

g. Reduced Irritation—My invention does not use adhesives and uses an inert material that comes in contact with the skin. The inert material, rounded contact surface, and reduced distributed forces that come in contact with the nasal cavity significantly reduces the probability of irritation.

h. Re-Useable—Unlike the prior art, this invention is re-useable and can be applied and removed as often as the user wishes. This is very advantageous when used at night or to satisfy intermittent short term needs.

i. Self Adjusting and Adjustable—My invention has two self adjusting features. The loop sections, tend to conform to the contour of the individual nostril vestibule. In addition, the spring rate is relatively constant over the deflection range. This produces a consistent and comparable force on a wide variety of nose sizes. The bend of the retaining tube can be increased or decreased to respectively increase the force on the against the vestibule wall. The user can also move the loops around to find the most comfortable and effective placement. As an additional adjustability feature, the inserted loop sizes can be adjusted by trimming the length or moved the lines in and out of the retaining tube.

j. Accommodate Wide Range of Nose Sizes—The looped shape of this invention along with the self adjusting feature from fully relaxed to fully bent positions and adjustability allows this invention to fit and operate effectively for a wide range of noses.

k. Economical—With the simplicity of design and the relative ease of manufacturing, this invention can be made more economical than prior art.

l. Easily Applied and Removed—My invention can be easily taken out and applied with one hand in the dark. This is a significant advantage over prior art.

m. Safe—Safety was a primary consideration in the design of this invention. It was designed to limit the penetration and area of contact inside the nasal cavity. The rounded contact surface and light contact force virtually eliminates any irritation to the user. It is also made from an inert material which does not react with human skin. The material is also flexible and smooth and is not abrasive to the sensitive nasal tissue.

n. Promotes Wellness—Quality of sleep affects both our mental and physical will being. My invention helps to reduce sleep disruptions resulting from excessive breathing through the mouth and nasal restrictions. The nose is designed to both condition the air we breathe by adding moisture and temperature. The nose also provides vital filtration to reduce harmful air particles and pollution from entering our lungs. My invention promotes nasal breathing and better filtration which results in more conditioning and filtration of the air we breathe. My invention therefore promotes wellness by improving sleep as well as the quality of air we breathe.

In addition to the above features, my invention also provides the option for the alternative health benefit claims of copper and magnetism. Since my invention has parts in contact with the skin, it can provide some of the same benefits as copper jewelry. Various forms of copper have been used for medicinal purposes throughout the history of mankind. The ancient Egyptian, Greek, Roman, Persian, Hindu and Aztec writings record various consistent medicinal uses of copper.

Today, as more information becomes available, alternative health care and home remedies are gaining popularity. Health publications now frequently include copper bracelets and copper jewelry as a home therapy remedy to ease the pain from arthritis and other joint problems. These benefits are found in many people who seem to get an insufficient amount of copper from their food. Several doctors who have studied this copper connection think the dissolved copper traces entering the body through the skin from a copper bracelet may be the only way for people to get the copper they need.

My invention also plans for an optional magnetic feature. Alternative medical studies have also made a number of claims concerning the benefits of magnets and magnetism. Some of the benefits that magnetic therapy claims to provide include: pain relief, reduction of swelling, improved tissue alkalinization, more restful sleep, increased tissue oxygenation, relief of stress, increased levels of cellular oxygen, improved blood circulation and anti-infective activity. Although my invention does not intend to provide the intensity and configuration of magnetism to gain all the benefits above, it does provide for an option to provide a small magnetic field for whatever benefit it may provide.

BRIEF SUMMARY OF INVENTION

My dilator filter provides a unique and alternative approach to improve nasal breathing, sleep, air filtration efficiency and reduced snoring. This present invention also addresses the disadvantages of prior art. My invention does not require adhesives, is reusable, can be easily adjusted for comfort and effectiveness, self adjusting to fit nose size variations, and requires less force on nasal tissue to reduce nasal air resistance. In addition, it does not cover the most visible part of the nose and provides a less noticeable appearance. These advantages in addition to the filtration efficiency improvement feature makes this invention unique to the prior art. My dilator filter provides a viable alternative for those who wish to use a mechanical device to improve nasal breathing, sleep, air filtration, and reduce snoring.

DETAILED DESCRIPTION OF THE INVENTION

Figure 1:
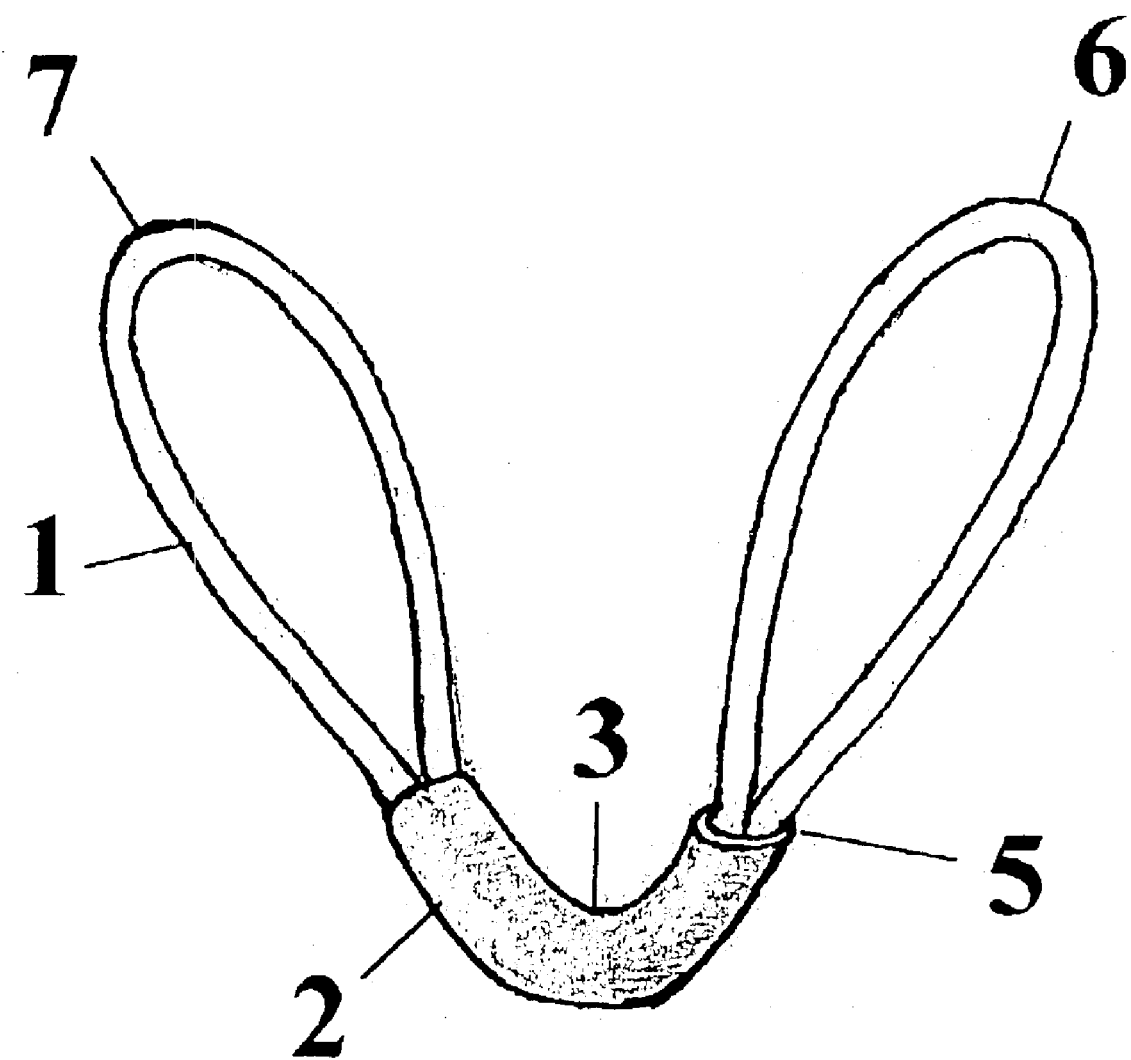
FIG. 1—Provides a perspective view of my invention.

My nasal dilator filter is shown in FIG. 1. This present invention is made from two components; a 0.050" diameter round standard nylon 11 line, 1, which can be varied in length from 4 to 5 inch long and a retainer, 2, made from a 0.5" long section of 0.125 OD standard nylon 11, brass or copper tube formed with a 0.125 inch inside diameter, 3. The single section of nylon line is inserted in the tube after a slight compression of the tube (retainer) and pulled through such that the retainer is in the middle of the length of nylon line. The ends of the line are then looped back into the retainer at 5, and inserted until the ends meet in the center of the retainer. The retainer is formed into a semicircle as depicted in the preferred embodiment in FIG. 1. The dimensions and configuration of the resulting loops are determined by the length of line and the bend of the retaining tube. The invention configuration consists of three sections; left loop, 7, retainer 2, and right loop, 6. The invention configuration is symmetrical with the left loop and right loop being essentially identical. The angle between the loop sections 6 and 7 is approximately 60 degrees. All dimensions may vary within normal manufacturing tolerances. The dimensions and configuration of the invention were designed to meet specific and unique operational objectives. FIG. 1 shows the present invention in normal relaxed form. The loops of the present invention are compressed between the fingers and inserted into the respective nostrils to exhibit its operational features discussed below. The loops are adjustable and can be varied in size by moving the end of the lines in and out of the retainer. The line can also be trimmed on each end and reinserted in the retaining tube to fit various nose sizes and configurations.

When inserted into the nostrils and into operating position, the retainer comes in contact with the tissue (skin covering the septal cartilage) separating the nostril openings, thereby limiting the depth of penetration into the respective nostrils. When in place, the loop sections are designed to operate just inside the nasal openings in what is called the vestibule of the nose. Although there are sensitive areas adjoining the vestibule of the nose. The present invention is designed to operate in an area of low sensitivity between the two nerve branches in the area (the interior nasal branch of the infraorbital nerve and the internal branch of the anterior ethmoidal nerve). The area of operation of this invention has less sensory nerves than the outer skin of the nose. When used properly this invention has been found to be more comfortable than the prior art. When inserted, the user will feel an immediate opening of the nostrils and a reduction in air resistance. The user can also move the end sections, within limits, for maximum effectiveness and comfort. The invention uses two methods to increase the flow area of the nostrils. The loop sections when inserted, tend to reform the vestibule area from a flat elliptical form into a more circular form thereby increasing the flow area. The loops also exhibit a force against the vestibule to further open the nasal passages. This force also increases the flow area by increasing the nasal valve opening. The magnitude of force is a function of the bend of the retainer and the length and diameter of the nylon line.

It is anticipated that the design presented in this specification will fit approximately 90% of adult nostrils. Other models are anticipated in essentially the same configuration but scaled up or down proportionally by varying the length of nylon line to fit noses in the smaller and larger end of the adult nostril size spectrum. The primary change to accommodate the different size nostrils is in the length of nylon line used and the resulting shorter of longer loops. Lines from 4 to 5.5 inches tend to cover the range of nostrils tested to date.

This invention can easily be manufactured and mass produced with readily available materials and processes. Current prototypes have been cut and assembled manually. Pilot user tests have been conducted along with clinical trials with excellent results.

What is claimed is:

1. A nasal dilator fitter comprising:
    a pair of adjacent adjustable generally symmetric loops configured to be inserted into respective nasal openings for improved nasal breathing and air filtration, wherein the loop material is negatively charged and readily gives up electrons to or attracts a portion of air particles and pollutants being inhaled through the nostrisl; and
    a retainer configured for securing, forming and positioning the loops adjacent one another and providing for adjustability to enable the relative dimensions of the loops to be adjusted.

2. A nasal dilator filter in accordance with claim 1 wherein the configuration and dimensions of the loops are determined by the length and physical characteristics of the loop material and the shape and connection to the retainer.

3. A nasal dilator filter in accordance with claim 1 wherein the loop size is variable and may be adjusted by moving a loop end in and out of the retainer and by varying the length of the loop material so that a wide range of nose sizes and configurations are accommodated.

4. A nasal dilator filter in accordance with claim 1 wherein the retainer comprises a tubular member dimensioned to receive and secure one end of one loop and to allow the other end of the loop to slide in and out in a press fit thereby accommodating adjustment of the size of a loop.

5. A nasal dilator filter in accordance with claim 1 wherein the retainer comprises a polymeric material or a metal containing copper or magnetic materials thereby providing the option of materials that provide alternative health benefits.

6. A nasal dilator filter in accordance with claim 1 wherein the loops each comprise an elongate polymeric material generally circular in cross-section dimensioned to minimize contact area and applied force inside the nasal cavity.

7. A nasal dilator filter in accordance with claim 1 wherein the loops are dimensioned to make contact in an area of low sensitivity between the two nerve branches (the interior nasal branch of the infraorbital nerve and the internal branch of the anterior ethmoidal nerve) inside the nasal cavity wherein the nasal air passage tissue is reshaped by reason of the force applied thereto by the loops so that nasal air passage resistance is reduced.

8. A nasal dilator filter in accordance with claim 1 wherein the loops exhibit a relatively constant spring rate over their entire deflection range and require deflection before inserting whereby an outward expanding force is exerted inside the nostrils adjacent a wearer's nasal valve.

9. A nasal dilator filter in accordance with claim 1 wherein a length of the respective loop is such that a tip of said loop is adjacent a wearer's nasal valve when inserted.

10. A nasal dilator filter in accordance with claim 1 wherein the loops exhibit mechanical and electrical properties similar to that of a nylon line with an approximate 0.050 inch substantially round cross section.

11. A nasal dilator filter in accordance with claim 1 wherein the loops, when inserted, expand the natural filtration surface area in the nasal cavity.

12. A nasal dilator filter in accordance with claim 1 wherein the loops comprise magnetic or copper materials thereby providing the option of materials that have alternative health benefits.

13. A nasal device which comprises a pair of generally symmetrically-shaped elongate tubular looped portions formed of a self-supporting, resiliently flexible polymeric material, each looped portion having an expanded distal bight end and a converging narrowed base proximal end adjacent which the looped portions are connected together so that the looped portions extend away from each other at an angle, wherein the bight portions are dimensioned and configured to be placed into each nostril opening of a user by applying a force thereto so as to resiliently deflect the bight portions toward each other, thereby decreasing the angle therebetween until the separation between the bight portions is such that they may be simultaneously inserted into the separate nostril openings of the user and thereafter, upon releasing the force applied thereto, caused to resiliently expand outwardly by reason of the resiliency of the material until the bight portions reach outwardly pressing engagement with the interior nasal cavity tissue, after which they continue to apply a desired amount of outward pressure to the tissue, the nasal device further comprising an elongate tubular connector open on its opposite ends to engagingly, releasably receive the proximal ends of said looped portions and, together with the boned portions, dimensioned to be disposed closely adjacent the skin covering the septal cartilage when the bight ends of the looped portions are inserted into the nostril openings in outwardly pressing engagement against the interior nasal tissue.

14. The device of claim 13, wherein at least one end of each looped portion is slidably, engageably received in the connector to enable adjustment of the length dimension of each looped portion.

15. The device of claim 13, wherein each looped portion is continuous.

16. The device of claim 13, wherein both looped portions comprise one continuous length of generally tubular material.

17. The device of claim 13, wherein the looped portions comprise solid nylon line.

* * * * *